US006436408B1

(12) United States Patent
Dowling et al.

(10) Patent No.: US 6,436,408 B1
(45) Date of Patent: *Aug. 20, 2002

(54) COLD-ADAPTED EQUINE INFLUENZA VIRUSES

(75) Inventors: Patricia W. Dowling; Julius S. Youngner, both of Pittsburgh, PA (US)

(73) Assignee: The University of Pittsburgh of the Commonwealth System of Higher Education, Pittsburgh, PA (US)

( * ) Notice: Subject to any disclaimer, the term of this patent is extended or adjusted under 35 U.S.C. 154(b) by 37 days.

This patent is subject to a terminal disclaimer.

(21) Appl. No.: 09/634,159

(22) Filed: Aug. 9, 2000

Related U.S. Application Data

(62) Division of application No. 09/133,921, filed on Aug. 13, 1998, now Pat. No. 6,177,082.

(51) Int. Cl.[7] .................... A61K 39/145; A61K 39/12; C12N 7/00; C12N 7/08; C12N 7/02
(52) U.S. Cl. .................... 424/209.1; 424/206.1; 424/204.1; 435/235.1; 435/237; 435/239
(58) Field of Search .................... 424/209.1, 206.1, 424/204.1; 435/235.1, 237, 239

(56) References Cited

U.S. PATENT DOCUMENTS

| | | | |
|---|---|---|---|
| 3,518,347 A | 6/1970 | Pavilanis et al. | 424/89 |
| 4,631,191 A | 12/1986 | Dale et al. | 424/88 |
| 4,683,137 A | 7/1987 | Coggins et al. | 424/89 |
| 4,693,893 A | 9/1987 | Campbell et al. | 424/89 |
| 4,920,213 A | 4/1990 | Dale et al. | 536/27 |
| 5,149,531 A | 9/1992 | Youngner et al. | 424/89 |
| 5,690,937 A | 11/1997 | Parkin et al. | 424/199.1 |

FOREIGN PATENT DOCUMENTS

| | | |
|---|---|---|
| WO | WO83/03546 | 10/1983 |
| WO | WO 92/00097 | 1/1992 |
| WO | WO 93/21310 | 10/1993 |
| WO | WO 00/09702 | 2/2000 |

OTHER PUBLICATIONS

Daly, et al., 1996, *Journal of General Virology*, vol. 77, pp. 661–671.
Lindstrom, et al., 1998, *Archives of Virology*, vol. 143, No. 8, pp. 1585–1598.
Brundage–Anguish, et al., 1982, *Am J Vet Res*, 43(5), pp. 869–874.
Enami, et al., 1990, *PNAS*, vol. 87, pp. 3802–3805.
Estola, et al., 1976, *Nord Vet med* vol. 28(7–8), pp. 353–356.
Hannant, et al., Feb. 6, 1988, *Vet Rec*, pp. 125–128.
Holmes, et al., 1992, Equine Infectious Diseases VI: Proceedings of the Sixth International Conference, Jul. 7–11, 1991, pp. 253–258.
Ilobi, et al., 1998, *Arch Virol*, vol. 143, pp. 891–901.
Kucera, et al., 1977, *Can J Comp Med*, 41(3), pp. 326–331.
Mumford, et al., 1983, *J Hyg (Lond)*, vol. 90(3), pp. 385–395.
Noble, et al., 1994, *J Gen Virol* vol. 75, pp. 3485–3491.
Reed, et al., 1938, *The American Journal of Hygiene*, vol. 27, pp. 493–497.
Timoney, P.J., 1996, *Comp Immunol Microbiol Infect Dis*, vol. 19(3), pp. 205–211.
USDA, 9 CFR 113.2XX, Oct. 28, 1994, Supplemental Assay Method for Conducting the Hemagglutination Inhibition Assay for Equine Influenza Antibody.
Van Maanen, et al., 1992, *Vet Q*, vol. 14(1), pp. 13–17.
Van Oirschot, et al., 1991, *Zentralbl Veterinarmed[B]*, vol. 38(5), pp. 391–396.
Wood, et al., 1983, *J Hyg(Lond)* vol. 90(3), pp. 371–384.
Wilson, et al., 1993, *Vet Clin North Am Equine Practi*, vol. 9(2), pp. 257–282.
Youngner, et al., 1994, *J. of Clinical of Microbiology*, vol. 32(3), pp. 750–754.
Lunn et al., 1999, *Vaccine*, vol. 17, pp. 2245–2258.
Romanova et al., 1997, *Vaccine*, vol. 15, No. 6/7, pp. 653–658.

*Primary Examiner*—Ali R. Salimi
(74) *Attorney, Agent, or Firm*—Heska Corporation

(57) ABSTRACT

The present invention provides experimentally-generated cold-adapted equine influenza viruses, and reassortant influenza A viruses comprising at least one genome segment of such an equine influenza virus, wherein the equine influenza virus genome segment confers at least one identifying phenotype of the cold-adapted equine influenza virus, such as cold-adaptation, temperature sensitivity, dominant interference, or attenuation. Such viruses are formulated into therapeutic compositions to protect animals from diseases caused by influenza A viruses, and in particular, to protect horses from disease caused by equine influenza virus. The present invention also includes methods to protect animals from diseases caused by influenza A virus utilizing the claimed therapeutic compositions. Such methods include using a therapeutic composition as a vaccine to generate a protective immune response in an animal prior to exposure to a virulent virus, and using a therapeutic composition as a treatment for an animal that has been recently infected with a virulent virus, or is likely to be subsequently exposed to virulent virus in a few days whereby the therapeutic composition interferes with the growth of the virulent virus, even in the absence of immunity. The present invention also provides methods to produce cold-adapted equine influenza viruses, and reassortant influenza A viruses having at least one genome segment of an equine influenza virus generated by cold-adaptation.

34 Claims, No Drawings

COLD-ADAPTED EQUINE INFLUENZA VIRUSES

This Application is a Divisional Application of application Ser. No. 09/133,921, filed Aug. 13, 1998, entitled "COLD-ADAPTED EQUINE INFLUENZA VIRUSES", which issued as U.S. Pat. No. 6,177,082 on Jan. 23, 2001.

FIELD OF THE INVENTION

The present invention relates to experimentally-generated cold-adapted equine influenza viruses, and particularly to cold-adapted equine influenza viruses having additional phenotypes, such as attenuation, dominant interference, or temperature sensitivity. The invention also includes reassortant influenza A viruses which contain at least one genome segment from such an equine influenza virus, such that the reassortant virus includes certain phenotypes of the donor equine influenza virus. The invention further includes genetically-engineered equine influenza viruses, produced through reverse genetics, which comprise certain identifying phenotypes of a cold-adapted equine influenza virus of the present invention. The present invention also relates to the use of these viruses in therapeutic compositions to protect animals from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, which has further diverged among Eurasian and North American isolates in recent years.

The currently licensed vaccine for equine influenza is an inactivated (killed) virus vaccine. This vaccine provides minimal, if any, protection for horses, and can produce undesirable side effects, for example, inflammatory reactions at the site of injection. See, e.g., Mumford, 1987, *Equine Infectious Disease IV*, 207–217, and Mumford, et al., 1993, *Vaccine* II, 1172–1174. Furthermore, current modalities cannot be used in young foals, because they cannot overcome maternal immunity, and can induce tolerance in a younger animal. Based on the severity of disease, there remains a need for safe, effective therapeutic compositions to protect horses against equine influenza disease.

Production of therapeutic compositions comprising cold-adapted human influenza viruses is described, for example, in Maassab, et al., 1960, *Nature* 7,612–614, and Maassab, et al., 1969, *J. Immunol.* 102, 728–732. Furthermore, these researchers noted that cold-adapted human influenza viruses, i.e., viruses that have been adapted to grow at lower than normal temperatures, tend to have a phenotype wherein the virus is temperature sensitive; that is, the virus does not grow well at certain higher, non-permissive temperatures at which the wild-type virus will grow and replicate. Various cold-adapted human influenza A viruses, produced by reassortment with existing cold-adapted human influenza A viruses, have been shown to elicit good immune responses in vaccinated individuals, and certain live attenuated cold-adapted reassortant human influenza A viruses have proven to protect humans against challenge with wild-type virus. See, e.g., Clements, et al., 1986, *J. Clin. Microbiol.* 23, 73–76. In U.S. Pat. No. 5,149,531, by Youngner, et al., issued Sep. 22, 1992, the inventors of the present invention further demonstrated that certain reassortant cold-adapted human influenza A viruses also possess a dominant interference phenotype, i.e., they inhibit the growth of their corresponding parental wild-type strain, as well as heterologous influenza A viruses.

U.S. Pat. No. 4,683,137, by Coggins et al., issued Jul. 28, 1987, and U.S. Pat. No. 4,693,893, by Campbell, issued Sep. 15, 1987, disclose attenuated therapeutic compositions produced by reassortment of wild-type equine influenza viruses with attenuated, cold-adapted human influenza A viruses. Although these therapeutic compositions appear to be generally safe and effective in horses, they pose a significant danger of introducing into the environment a virus containing both human and equine influenza genes.

SUMMARY OF THE INVENTION

The present invention provides experimentally-generated cold-adapted equine influenza viruses, reassortant influenza A viruses that comprise at least one genome segment of an equine influenza virus generated by cold-adaptation such that the equine influenza virus genome segment confers at least one identifying phenotype of a cold-adapted equine influenza virus on the reassortant virus, and genetically-engineered equine influenza viruses, produced through reverse genetics, which comprise at least one identifying phenotype of a cold-adapted equine influenza virus. Identifying phenotypes include cold-adaptation, temperature sensitivity, dominant interference, and attenuation. The invention further provides a therapeutic composition to protect an animal against disease caused by an influenza A virus, where the therapeutic composition includes a cold-adapted equine influenza virus a reassortant influenza A virus, or a genetically-engineered equine influenza virus of the present invention. Also provided is a method to protect an animal from diseases caused by an influenza A virus which includes the administration of such a therapeutic composition. Also provided are methods to produce a cold-adapted equine influenza virus, and methods to produce a reassortant influenza A virus which comprises at least one genome segment of a cold-adapted equine influenza virus, where the equine influenza genome segment confers on the reassortant virus at least one identifying phenotype of the cold-adapted equine influenza virus.

A cold-adapted equine influenza virus is one that replicates in embryonated chicken eggs at a temperature ranging from about 26° C. to about 30° C. Preferably, a cold-adapted equine influenza virus, reassortant influenza A virus, or genetically-engineered equine influenza virus of the present invention is attenuated, such that it will not cause disease in a healthy animal.

In one embodiment, a cold-adapted equine influenza virus, reassortant influenza A virus, or genetically-engineered equine influenza virus of the present invention is also temperature sensitive, such that the virus replicates in embryonated chicken eggs at a temperature ranging from about 26° C. to about 30° C., forms plaques in tissue culture cells at a permissive temperature of about 34° C., but does not form plaques in tissue culture cells at a non-permissive temperature of about 39° C.

In one embodiment, such a temperature sensitive virus comprises two mutations: a first mutation that inhibits plaque formation at a temperature of about 39° C., that mutation co-segregating with the genome segment that encodes the viral nucleoprotein gene; and a second mutation that inhibits all viral protein synthesis at a temperature of about 39° C.

In another embodiment, a cold-adapted, temperature sensitive equine influenza virus of the present invention replicates in embryonated chicken eggs at a temperature ranging from about 26° C. to about 30° C., forms plaques in tissue culture cells at a permissive temperature of about 34° C., but does not form plaques in tissue culture cells or express late viral proteins at a non-permissive temperature of about 37° C.

Typically, a cold-adapted equine influenza virus of the present invention is produced by passaging a wild-type equine influenza virus one or more times, and then selecting viruses that stably grow and replicate at a reduced temperature. A cold-adapted equine influenza virus produced thereby includes, in certain embodiments, a dominant interference phenotype, that is, the virus, when co-infected with a parental equine influenza virus or heterologous wild-type influenza A virus, will inhibit the growth of that virus.

Examples of cold-adapted equine influenza viruses of the present invention include EIV-P821, identified by accession No. ATCC VR-2625; EIV-P824, identified by accession No. ATCC VR-2624; EIV-MSV+5, identified by accession No. ATCC VR-2627; and progeny of such viruses.

Therapeutic compositions of the present invention include from about $10^5$ $TCID_{50}$ units to about $10^8$ $TCID_{50}$ units, and preferably about $2 \times 10^6$ $TCID_{50}$ units, of a cold-adapted equine influenza virus, reassortant influenza A virus, or genetically-engineered equine influenza virus of the present invention.

The present invention also includes a method to protect an animal from disease caused by an influenza A virus, which includes the step of administering to the animal a therapeutic composition including a cold-adapted equine influenza virus, a reassortant influenza A virus, or a genetically-engineered equine influenza virus of the present invention. Preferred animals to protect include equids, with horses and ponies being particularly preferred.

Yet another embodiment of the present invention is a method to generate a cold-adapted equine influenza virus. The method includes the steps of passaging a wild-type equine influenza virus; and selecting viruses that grow at a reduced temperature. In one embodiment, the method includes repeating the passaging and selection steps one or more times, while progressively reducing the temperature. Passaging of equine influenza virus preferably takes place in embryonated chicken eggs.

Another embodiment is an method to produce a reassortant influenza A virus through genetic reassortment of the genome segments of a donor cold-adapted equine influenza virus of the present invention with the genome segments of a recipient influenza A virus. Reassortant influenza A viruses of the present invention are produced by a method that includes the steps of: (a) mixing the genome segments of a donor cold-adapted equine influenza virus with the genome segments of a recipient influenza A virus, and (b) selecting viruses which include at least one identifying phenotype of the donor equine influenza virus. Identifying phenotypes include cold-adaptation, temperature sensitivity, dominant interference, and attenuation. Preferably, such reassortant viruses at least include the attenuation phenotype of the donor virus. A typical reassortant virus will have the antigenicity of the recipient virus, that is, it will retain the hemagglutinin (HA) and neuraminidase (NA) phenotypes of the recipient virus.

The present invention further provides methods to propagate cold-adapted equine influenza viruses or reassortant influenza A viruses of the present invention. These methods include propagation in embryonated chicken eggs or in tissue culture cells.

DETAILED DESCRIPTION OF THE INVENTION

The present invention provides experimentally-generated cold-adapted equine influenza viruses comprising certain defined phenotypes, which are disclosed herein. It is to be noted that the term "a" or "an" entity, refers to one or more of that entity; for example, "a cold-adapted equine influenza virus" can include one or more cold-adapted equine influenza viruses. As such, the terms "a" (or "an"), "one or more," and "at least one" can be used interchangeably herein. It is also to be noted that the terms "comprising," "including," and "having" can be used interchangeably. Furthermore, an item "selected from the group consisting of" refers to one or more of the items in that group, including combinations thereof.

A cold-adapted equine influenza virus of the present invention is a virus that has been generated in the laboratory, and as such, is not a virus as occurs in nature. Since the present invention also includes those viruses having the identifying phenotypes of such a cold-adapted equine influenza virus, an equine influenza virus isolated from a mixture of naturally-occurring viruses, i.e., removed from its natural milieu, but having the claimed phenotypes, is included in the present invention. A cold-adapted equine influenza virus of the present invention does not require any specific level of purity. For example, a cold-adapted equine influenza virus grown in embryonated chicken eggs may be in a mixture with the allantoic fluid (AF), and a cold-adapted equine influenza virus grown in tissue culture cells may be in a mixture with disrupted cells and tissue culture medium.

As used herein, an "equine influenza virus" is an influenza virus that infects and grows in equids, e.g., horses or ponies. As used herein, "growth" of a virus denotes the ability of the virus to reproduce or "replicate" itself in a permissive host cell. As such, the terms, "growth of a virus" and "replication of a virus" are used interchangeably herein. Growth or replication of a virus in a particular host cell can be demonstrated and measured by standard methods well-known to those skilled in the art of virology. For example, samples containing infectious virus, e.g., as contained in nasopharyngeal secretions from an infected horse, are tested for their ability to cause cytopathic effect (CPE), e.g., virus plaques, in tissue culture cells. Infectious virus may also be detected by inoculation of a sample into the allantoic cavity of embryonated chicken eggs, and then testing the AF of eggs thus inoculated for its ability to agglutinate red blood cells, i.e., cause hemagglutination, due to the presence of the influenza virus hemagglutinin (HA) protein in the AF.

Naturally-occurring, i.e., wild-type, equine influenza viruses replicate well at a temperature from about 34° C. to about 39° C. For example, wild-type equine influenza virus replicates in embryonated chicken eggs at a temperature of about 34° C., and replicates in tissue culture cells at a temperature from about 34° C. to about 39° C. As used herein, a "cold-adapted" equine influenza virus is an equine influenza virus that has been adapted to grow at a temperature lower than the optimal growth temperature for equine influenza virus. One example of a cold-adapted equine influenza virus of the present invention is a virus that replicates in embryonated chicken eggs at a temperature of about 30° C. A preferred cold-adapted equine influenza virus of the present invention replicates in embryonated chicken eggs at a temperature of about 28° C. Another preferred cold-adapted equine influenza virus of the present invention replicates in embryonated chicken eggs at a temperature of about 26° C. In general, preferred cold-adapted equine influenza viruses of the present invention replicate in embryonated chicken eggs at a temperature ranging from about 26° C. to about 30° C., i.e., at a range of temperatures at which a wild-type virus will grow poorly or not at all. It should be noted that the ability of such viruses to replicate within that temperature range does not preclude their ability to also replicate at higher or lower temperatures. For example, one embodiment is a cold-adapted equine influenza virus that replicates in embryonated chicken eggs at a temperature of about 26° C., but also replicates in tissue culture cells at a temperature of about 34° C. As with wild-type equine influenza viruses, cold-adapted equine influenza viruses of the present invention generally form plaques in tissue culture cells, for example Madin Darby Canine Kidney Cells (MDCK) at a temperature of about 34° C. Examples of suitable and preferred cold-adapted equine influenza viruses of the present invention are disclosed herein.

One embodiment of the present invention is a cold-adapted equine influenza virus that is produced by a method which includes passaging a wild-type equine influenza virus, and then selecting viruses that grow at a reduced temperature. Cold-adapted equine influenza viruses of the present invention can be produced, for example, by sequentially passaging a wild-type equine influenza virus in embryonated chicken eggs at progressively lower temperatures, thereby selecting for certain members of the virus mixture which stably replicate at the reduced temperature. An example of a passaging procedure is disclosed in detail in the Examples section. During the passaging procedure, one or more mutations appear in certain of the single-stranded RNA segments comprising the influenza virus genome, which alter the genotype, i.e., the primary nucleotide sequence of those RNA segments. As used herein, a "mutation" is an alteration of the primary nucleotide sequence of any given RNA segment making up an influenza virus genome. Examples of mutations include substitution of one or more nucleotides, deletion of one or more nucleotides, insertion of one or more nucleotides, or inversion of a stretch of two or more nucleotides. By selecting for those members of the virus mixture that stably replicate at a reduced temperature, a virus with a cold-adaptation phenotype is selected. As used herein, a "phenotype" is an observable or measurable characteristic of a biological entity such as a cell or a virus, where the observed characteristic is attributable to a specific genetic configuration of that biological entity, i.e., a certain genotype. As such, a cold-adaptation phenotype is the result of one or more mutations in the virus genome. As used herein, the terms "a mutation," "a genome," "a genotype," or "a phenotype" refer to one or more, or at least one mutation, genome, genotype, or phenotype, respectively.

Additional, observable phenotypes in a cold-adapted equine influenza virus may occur, and will generally be the result of one or more additional mutations in the genome of such a virus. For example, a cold-adapted equine influenza virus of the present invention may, in addition, be attenuated, exhibit dominant interference, and/or be temperature sensitive.

In one embodiment, a cold-adapted equine influenza virus of the present invention has a phenotype characterized by attenuation. A cold-adapted equine influenza virus is "attenuated," when administration of the virus to an equine influenza virus-susceptible animal results in reduced or absent clinical signs in that animal, compared to clinical signs observed in animals that are infected with wild-type equine influenza virus. For example, an animal infected with wild-type equine influenza virus will display fever, sneezing, coughing, depression, and nasal discharges. In contrast, an animal administered an attenuated, cold-adapted equine influenza virus of the present invention will display minimal or no, i.e., undetectable, clinical disease signs.

In another embodiment, a cold-adapted equine influenza virus of the present invention comprises a temperature sensitive phenotype. As used herein, a temperature sensitive cold-adapted equine influenza virus replicates at reduced temperatures, but no longer replicates or forms plaques in tissue culture cells at certain higher growth temperatures at which the wild-type virus will replicate and form plaques. While not being bound by theory, it is believed that replication of equine influenza viruses with a temperature sensitive phenotype is largely restricted to the cool passages of the upper respiratory tract, and does not replicate efficiently in the lower respiratory tract, where the virus is more prone to cause disease symptoms. A temperature at which a temperature sensitive virus will grow is referred to herein as a "permissive" temperature for that temperature sensitive virus, and a higher temperature at which the temperature sensitive virus will not grow, but at which a corresponding wild-type virus will grow, is referred to herein as a "non-permissive" temperature for that temperature sensitive virus. For example, certain temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non-permissive temperature of about 39° C. Other temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non-permissive temperature of about 37° C.

Certain cold-adapted equine influenza viruses of the present invention have a dominant interference phenotype; that is, they dominate an infection when co-infected into cells with another influenza A virus, thereby impairing the growth of that other virus. For example, when a cold-adapted equine influenza virus of the present invention, having a dominant interference phenotype, is co-infected into MDCK cells with the wild-type parental equine influenza virus, A/equine/Kentucky/1/91 (H3N8), growth of the parental virus is impaired. Thus, in an animal that has recently been exposed to, or may be soon exposed to, a virulent influenza virus, i.e., an influenza virus that causes disease symptoms, administration of a therapeutic composition comprising a cold-adapted equine influenza virus having a dominant interference phenotype into the upper respiratory tract of that animal will impair the growth of the virulent virus, thereby ameliorating or reducing disease in that animal, even in the absence of an immune response to the virulent virus.

Dominant interference of a cold-adapted equine influenza virus having a temperature sensitive phenotype can be measured by standard virological methods. For example, separate monolayers of MDCK cells can be infected with (a) a virulent wild-type influenza A virus, (b) a temperature sensitive, cold-adapted equine influenza virus, and (c) both viruses in a co-infection, with all infections done at multiplicities of infection (MOI) of about 2 plaque forming units (pfu) per cell. After infection, the virus yields from the various infected cells are measured by duplicate plaque assays performed at the permissive temperature for the cold-adapted equine influenza virus and at the non-permissive temperature of that virus. A cold adapted equine influenza virus having a temperature sensitive phenotype is unable to form plaques at its non-permissive temperature, while the wild-type virus is able to form plaques at both the permissive and non-permissive temperatures. Thus it is possible to measure the growth of the wild-type virus in the presence of the cold adapted virus by comparing the virus yield at the non-permissive temperature of the cells singly infected with wild-type virus to the yield at the non-permissive temperature of the wild-type virus in doubly infected cells.

Cold-adapted equine influenza viruses of the present invention are characterized primarily by one or more of the following identifying phenotypes: cold-adaptation, temperature sensitivity, dominant interference, and/or attenuation. As used herein, the phrase "an equine influenza virus comprises, the identifying phenotype(s) of cold-adaptation, temperature sensitivity, (dominant interference, and/or attenuation" refers to a virus having such a phenotype(s). Examples of such viruses include, but are not limited to, EIV-P821, identified by accession No. ATCC VR-2625, EIV-P824, identified by accession No. ATCC VR-2624, and EIV-MSV+5, identified by accession No, ATCC VR-2627, as well as EIV-MSVO, EIV, MSV+1, EIV-MSV+2, EIV-MSV+3, and EIV-MSV+4. Production of such viruses is described in the examples. For example, cold-adapted equine influenza virus EIV-P821 is characterized by, i.e., has the identifying phenotypes of, (a) cold-adaptation, e.g., its ability to replicate in embryonated chicken eggs at a temperature of about 26° C.; (b) temperature sensitivity, e.g., its inability to form plaques in tissue culture cells and to express late gene products at a non-permissive temperature of about 37° C., and its inability to form plaques in tissue culture cells and to synthesize any viral proteins at a non-permissive temperature of about 39° C.; (c) its attenuation upon administration to an equine influenza virus-susceptible animal; and (d) dominant interference, e.g., its ability, when co-infected into a cell with a wild-type influenza A virus, to interfere with the growth of that wild-type virus. Similarly, cold-adapted equine influenza virus EIV-P824 is characterized by (a) cold adaptation, e.g., its ability to replicate in embryonated chicken eggs at a temperature of about 28° C.; (b) temperature sensitivity, e.g., its inability to form plaques in tissue culture cells at a non-permissive temperature of about 39° C.; and (c) dominant interference, e.g., its ability, when co-infected into a cell with a wild-type influenza A virus, to interfere with the growth of that wild-type virus. In another example, cold-adapted equine influenza virus EIV-MSV+5 is characterized by (a) cold-adaptation, e.g., its ability to replicate in embryonated chicken eggs at a temperature of about 26° C.; (b) temperature sensitivity, e.g., its inability to form plaques in tissue culture cells at a non-permissive temperature of about 39° C.; and (c) its attenuation upon administration to an equine influenza virus-susceptible animal.

In certain cases, the RNA segment upon which one or more mutations associated with a certain phenotype occur may be determined through reassortment analysis by standard methods, as disclosed herein. In one embodiment, a cold-adapted equine influenza virus of the present invention comprises a temperature sensitive phenotype that correlates with at least two mutations in the genome of that virus. In this embodiment, one of the two mutations, localized by reassortment analysis as disclosed herein, inhibits, i.e., blocks or prevents, the ability of the virus to form plaques in tissue culture cells at a non-permissive temperature of about 39° C. This mutation co-segregates with the segment of the equine influenza virus genome that encodes the nucleoprotein (NP) gene of the virus, i.e., the mutation is located on the same RNA segment as the NP gene. In this embodiment, the second mutation inhibits all protein synthesis at a non-permissive temperature of about 39° C. As such, at the non-permissive temperature, the virus genome is incapable of expressing any viral proteins. Examples of cold-adapted equine influenza viruses possessing these characteristics are EIV-P821 and EIV MSV+5. EIV-P821 was generated by serial passaging of a wild-type equine influenza virus in embryonated chicken eggs by methods described in Example 1A. EIV-MSV+5 was derived by further serial passaging of EIV-P821, as described in Example 1E.

Furthermore, a cold-adapted, temperature sensitive equine influenza virus comprising the two mutations which inhibit plaque formation and viral protein synthesis at a non-permissive temperature of about 39° C. can comprise one or more additional mutations, which inhibit the virus' ability to synthesize late gene products and to form plaques in tissue culture cells at a non-permissive temperature of about 37° C. An example of a cold-adapted equine influenza virus possessing these characteristics is EIV-P821. This virus isolate replicates in embryonated chicken eggs at a temperature of about 26° C., and does not form plaques or express any viral proteins at a temperature of about 39° C. Furthermore, EIV-P821 does not form plaques on MDCK cells at a non-permissive temperature of about 37° C., and at this temperature, late gene expression is inhibited in such a way that late proteins are not produced, i.e., normal levels of NP protein are synthesized, reduced or undetectable levels of M1 or HA proteins are synthesized, and enhanced levels of the polymerase proteins are synthesized. Since this phenotype is typified by differential viral protein synthesis, it is distinct from the protein synthesis phenotype seen at a non-permissive temperature of about 39° C., which is typified by the inhibition of synthesis of all viral proteins.

Pursuant to 37 CFR § 1.802 (a-c), cold-adapted equine influenza viruses, designated herein as EIV-P821, an EIV-P824 were deposited with the American Type Culture Collection (ATCC, 10801 University Boulevard, Manassas, Va. 20110-2209) under the Budapest Treaty as ATCC Accession Nos. ATCC VR-2625, and ATCC VR-2624, respectively, on Jul. 11, 1998. Cold-adapted equine influenza virus EIV-MSV+5 was deposited with the ATCC as ATCC Accession No. ATCC VR-2627 on Aug. 3, 1998. Pursuant to 37 CFR§ 1.806, the deposits are made for a term of at least thirty (30) years and at least five (5) years after the most recent request for the furnishing of a sample of the deposit was received by the depository. Pursuant to 37 CFR § 1.808 (a)(2), all restrictions imposed by the depositor on the availability to the public will be irrevocably removed upon the granting of the patent.

Preferred cold-adapted equine influenza viruses of the present invention have the identifying phenotypes of EIV-P821, EIV-P824, and EIV-MSV+5. Particularly preferred cold-adapted equine influenza viruses include EIV-P821, EIV-P824, EIV-MSV+5, and progeny of these viruses. As used herein, "progeny" are "offspring," and as such can slightly altered phenotypes compared to the parent virus, but retain identifying phenotypes of the parent virus, for example, cold-adaptation, temperature sensitivity, dominant interference, or attenuation. For example, cold-adapted equine influenza virus EIV-MSV+5 is a "progeny" of cold-adapted equine influenza virus EIV-P821. "Progeny" also include reassortant influenza A viruses that comprise one or more identifying phenotypes of the donor parent virus.

Reassortant influenza A viruses of the present invention are produced by genetic reassortment of the genome segments of a donor cold-adapted equine influenza virus of the present invention with the genome segments of a recipient influenza A virus, and then selecting a reassortant virus that derives at least one of its eight RNA genome segments from the donor virus, such that the reassortant virus acquires at least one identifying phenotype of the donor cold-adapted equine influenza virus. Identifying phenotypes include cold-adaptation, temperature sensitivity, attenuation, and dominant interference. Preferably, reassortant influenza A viruses of the present invention derive at least the attenuation phenotype of the donor virus. Methods to isolate reassortant influenza viruses are well known to those skilled in the art of virology and are disclosed, for example, in Fields, et al., 1996, *Fields Virology*, 3d ed., Lippincott-Raven; and Palese, et al., 1976, *J. Virol.*, 17, 876–884. Fields, et al., ibid. and Palese, et al., ibid. are incorporated herein by reference in their entireties. A suitable donor equine influenza, virus is a cold-adapted equine influenza virus of the present invention, for example, EIV-P821, identified by accession No. ATCC VR-2625, EIV-P824, identified by accession No. ATCC VR-2624, or EIV-MSV+5, identified by accession No. ATCC VR-2627. A suitable recipient influenza A virus can be another equine influenza virus, for example a Eurasian subtype 2 equine influenza virus such as A/equine/Suffolk/89 (H3N8) or a subtype 1 equine influenza virus such a, A/Prague/1/56 (H7N7). A recipient influenza A virus can also be any influenza A virus capable of forming a reassortant virus with a donor cold-adapted equine influenza virus. Examples of such influenza A viruses include, but are not limited to, human influenza viruses such as A/Puerto Rico/8/34 (H1N1), A/Hong Kong/156/97 (H5N1), A/Singapore/1/57 (H2N2), and A/Hong Kong/1/68 (H3N2); swine viruses such as A/Swine/Iowa/15/30 (H1N1); and avian viruses such as A/mallard/New York/6750/78 (H2N2) and A/chicken/Hong Kong/258/97 (H5N1). A reassortant virus of the present invention can include any combination of donor and recipient gene segments, as long as the resulting reassortant virus possesses at least one identifying phenotype of the donor virus.

One example of a reassortant virus of the present invention is a "6+2" reassortant virus, in which the six "internal gene segments," i.e., those comprising the NP, PB2, PB1, PA, M, and NS genes, are derived from the donor cold-adapted equine influenza virus genome, and the two "external gene segments," i.e., those comprising the HA and NA genes, are derived from the recipient influenza A virus. A resultant virus thus produced has the attenuated, cold-adapted, temperature sensitive, and/or dominant interference phenotypes of the donor cold-adapted equine influenza virus, but the antigenicity of the recipient strain.

In yet another embodiment, a cold-adapted equine influenza virus of the present invention can be produced through recombinant means. In this approach, one or more specific mutations, associated with identified cold-adaptation, attenuation, temperature sensitivity, or dominant interference phenotypes, are identified and are introduced back into a wild-type equine influenza virus strain using a reverse genetics approach. Reverse genetics entails using RNA polymerase complexes isolated from influenza virus-infected cells to transcribe artificial influenza virus genome segments containing the mutation(s), incorporating the synthesized RNA segment(s) into virus particles using a helper virus, and then selecting for viruses containing the desired changes. Reverse genetics methods for influenza viruses are described, for example, in Enami, et al., 1990, *Proc. Natl. Acad. Sci.* 87, 3802–3805; and in U.S. Pat. No. 5,578,473, by Palese, et al., issued Nov. 26, 1996, both of which are incorporated herein by reference in their entireties. This approach allows one skilled in the art to produce additional cold-adapted equine influenza viruses of the present invention without the need to go through the lengthy cold-adaptation process, and the process of selecting mutants both in vitro and in vivo with the desired virus phenotype.

A cold-adapted equine influenza virus of the present invention may be propagated by standard virological methods well-known to those skilled in the art, examples of which are disclosed herein. For example, a cold-adapted equine influenza virus can be grown in embryonated chicken eggs or in eukaryotic tissue culture cells. Suitable continuous eukaryotic cell lines upon which to grow a cold-adapted equine influenza virus of the present invention include those that support growth of influenza viruses, for example, MDCK cells. Other suitable cells upon which to grow a cold-adapted equine influenza virus of the present invention include, but are not limited to, primary kidney cell cultures of monkey, calf, hamster or chicken.

In one embodiment, the present invention provides a therapeutic composition to protect an animal against disease caused by an influenza A virus, where the therapeutic composition includes either a cold-adapted equine influenza virus or a reassortant influenza A virus comprising at least one genome segment of an equine influenza virus generated by cold-adaptation, wherein the equine influenza virus genome segment confers at least one identifying phenotype of the cold-adapted equine influenza virus. In addition, a therapeutic composition of the present invention can include an equine influenza virus that has been genetically engineered to comprise one or more mutations, where those mutations have been identified to confer a certain identifying phenotype on a cold-adapted equine influenza virus of the present invention. As used herein, the phrase "disease caused by an influenza A virus" refers to the clinical manifestations observed in an animal which has been infected with a virulent influenza A virus. Examples of such clinical manifestations include, but are not limited to, fever, sneezing, coughing, nasal discharge, rales, anorexia and depression. In addition, the phrase "disease caused by an influenza A virus" is defined herein to include shedding of virulent virus by the infected animal. Verification that clinical manifestations observed in an animal correlate with infection by virulent equine influenza virus may be made by several methods, including the detection of a specific antibody and/or T-cell responses to equine influenza virus in the animal. Preferably, verification that clinical manifestations observed in an animal correlate with infection by a virulent influenza A virus is made by the isolation of the virus from the afflicted animal, for example, by swabbing the nasopharyngeal cavity of that animal for virus-containing secretions. Verification of virus isolation may be made by the detection of CPE in tissue culture cells inoculated with the isolated secretions, by inoculation of the isolated secretions into embryonated chicken eggs, where virus replication is detected by the ability of AF from the inoculated eggs to agglutinate erythrocytes, suggesting the presence of the influenza virus hemagglutinin protein, or by use of a commercially available diagnostic test, for example, the Directigen® FLU A test.

As used herein, the term "to protect" includes, for example, to prevent or to treat influenza A virus infection in the subject animal. As such, a therapeutic composition of the present invention can be used, for example, as a prophylactic vaccine to protect a subject animal from influenza disease by administering the therapeutic composition to that animal at some time prior to that animal's exposure to the virulent virus.

A therapeutic composition of the present invention, comprising a cold-adapted equine influenza virus having a dominant interference phenotype, can also be used to treat an animal that has been recently infected with virulent influenza A virus or is likely to be subsequently exposed in a few days, such that the therapeutic composition immediately interferes with the growth of the virulent virus, prior to the animal's production of antibodies to the virulent virus. A therapeutic composition comprising a cold-adapted equine influenza virus having a dominant interference phenotype may be effectively administered prior to subsequent exposure for a length of time corresponding to the approximate length of time that a cold-adapted equine influenza virus of the present invention will replicate in the upper respiratory tract of a treated animal, for example, up to about seven days. A therapeutic composition comprising a cold-adapted equine influenza virus having a dominant interference phenotype may be effectively administered following exposure to virulent equine influenza virus for a length of time corresponding to the time required for an infected animal to show disease symptoms, for example, up to about two days.

Therapeutic compositions of the present invention can be administered to any animal susceptible to influenza virus disease, for example, humans, swine, horses and other equids, aquatic birds, domestic and game fowl, seals, mink, and whales. Preferably, a therapeutic composition of the present invention is administered equids. Even more preferably, a therapeutic composition of the present invention is administered to a horse, to protect against equine influenza disease.

Current vaccines available to protect horses against equine influenza virus disease are not effective in protecting young foals, most likely because they cannot overcome the maternal antibody present in these young animals, and often, vaccination at an early age, for example 3 months of age, can lead to tolerance rather than immunity. In one embodiment, and in contrast to existing equine influenza virus vaccines, a therapeutic composition comprising a cold-adapted equine influenza virus of the present invention apparently can produce immunity in young animals. As such, a therapeutic composition of the present invention can be safely and effectively administered to young foals, as young as about 3 months of age, to protect against equine influenza disease without the induction of tolerance.

In one embodiment, a therapeutic composition of the present invention can be multivalent. For example, it can protect an animal from more than one strain of influenza A virus by providing a combination of one or more cold-adapted equine influenza viruses of the present invention, one or more reassortant influenza A viruses, and/or one or more genetically-engineered equine influenza viruses of the present invention. Multivalent therapeutic compositions can include at least two cold-adapted equine influenza viruses, e.g., against North American subtype-2 virus isolates such as A/equine/Kentucky/1/91 (H1N8), and Eurasian subtype-2 virus isolates such as A/equine/Suffolk/89 (H3N8); or one or more subtype-2 virus isolates and a subtype-1 virus isolate such as A/equine/Prague/1/56 (H7N7). Similarly, a multivalent therapeutic composition of the present invention can include a cold-adapted equine influenza virus and a reassortant influenza A virus of the present invention, or two reassortant influenza A viruses of the present invention. A multivalent therapeutic composition of the present invention can also contain one or more formulations to protect against one or more other infectious agents in addition to influenza A virus. Such other infectious agents include, but not limited to: viruses; bacteria; fungi and fungal-related microorganisms; and parasites. Preferable multivalent therapeutic compositions include, but are not limited to, a cold-adapted equine influenza virus, reassortant influenza A virus, or genetically-engineered equine influenza virus of the present invention plus one or more compositions protective against one or more other infectious agents that afflict horses. Suitable infectious agents to protect against include, but are not limited to, equine infectious anemia virus, equine herpes virus, eastern, western, or Venezuelan equine encephalitis virus, tetanus, *Streptococcus equi*, and *Ehrlichia resticii*.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability.

Examples of buffers include phosphate buffer, bicarbonate buffer, and Tris buffer, while examples of stabilizers include A1/A2 stabilizer, available from Diamond Animal Health, Des Moines, Iowa. Standard formulations can either be liquids or solids which can be taken up in a suitable liquid as a suspension or solution for administration to an animal. In one embodiment, a non-liquid formulation may comprise the excipient salts, buffers, stabilizers, etc., to which sterile water or saline can be added prior to administration.

A therapeutic composition of the present invention may also include one or more adjuvants or carriers. Adjuvants are typically substances that enhance the immune response of an animal to a specific antigen, and carriers include those compounds that increase the half-life of a therapeutic composition in the treated animal. One advantage of a therapeutic composition comprising a cold-adapted equine influenza virus or a reassortant influenza A virus of the present invention is that adjuvants and carriers are not required to produce an efficacious vaccine. Furthermore, in many cases known to those skilled in the art, the advantages of a therapeutic composition of the present invention would be hindered by the use of some adjuvants or carriers. However, it should be noted that use of adjuvants or carriers is not precluded by the present invention.

Therapeutic compositions of the present invention include an amount of a cold-adapted equine influenza virus that is sufficient to protect an animal from challenge with virulent equine influenza virus. In one embodiment, a therapeutic composition of the present invention can include an amount of a cold-adapted equine influenza virus ranging from about $10^5$ tissue culture infectious dose-50 ($TCID_{50}$) units of virus to about $10^8$ $TCID_{50}$ units of virus. As used herein, a "$TCID_{50}$ unit" is amount of a virus which results in cytopathic effect in 50% of those cell cultures infected. Methods to measure and calculate $TCID_{50}$ are known to those skilled in the art and are available, for example, in Reed and Muench, 1938, *Am. J. of Hyg.* 27,493–497, which is incorporated herein by reference in its entirety. A preferred therapeutic composition of the present invention comprises from about $10^6$ $TCID_{50}$ units to about $10^7$ $TCID_{50}$ units of a cold-adapted equine influenza virus or reassortant influenza A virus of the present invention. Even more preferred is a therapeutic composition comprising about $2\times10^6$ TCID$_{50}$ units of a cold-adapted equine influenza virus or reassortant influenza A virus of the present invention.

The present invention also includes methods to protect an animal against disease caused by an influenza A virus comprising administering to the animal a therapeutic composition of the present invention. Preferred are those methods which protect an equid against disease caused by equine influenza virus, where those methods comprise administering to the equid a cold-adapted equine influenza virus. Acceptable protocols to administer therapeutic compositions in an effective manner include individual dose size, number of doses, frequency of dose administration, and mode of administration. Determination of such protocols can be accomplished by those skilled in the art, and examples are disclosed herein.

A preferable method to protect an animal against disease caused by an influenza A virus includes administering to that animal a single dose of a therapeutic composition comprising a cold-adapted equine influenza virus, a reassortant influenza A virus, or genetically-engineered equine influenza virus of the present invention. A suitable single dose is a dose that is capable of protecting an animal from disease when administered one or more times over a suitable time period. The method of the present invention may also include administering subsequent, or booster doses of a therapeutic composition. Booster administrations can be given from about 2 weeks to several years after the original administration. Booster administrations preferably are administered when the immune response of the animal becomes insufficient to protect the animal from disease. Examples of suitable and preferred dosage schedules are disclosed in the Examples section.

A therapeutic composition of the present invention can be administered to an animal by a variety of means, such that the virus will enter and replicate in the mucosal cells in the upper respiratory tract of the treated animal. Such means include, but are not limited to, intranasal administration, oral administration, and intraocular administration. Since influenza viruses naturally infect the mucosa of the upper respiratory tract, a preferred method to administer a therapeutic composition of the present invention is by intranasal administration. Such administration may be accomplished by use of a syringe fitted with cannula, or by use of a nebulizer fitted over the nose and mouth of the animal to be vaccinated.

The efficacy of a therapeutic composition of the present invention to protect an animal against disease caused by influenza A virus can be tested in a variety of ways including, but not limited to, detection of antibodies by, for example, hemagglutination inhibition (HAI) tests, detection of cellular immunity within the treated animal, or challenge of the treated animal with virulent equine influenza virus to determine whether the treated animal is resistant to the development of disease. In addition, efficacy of a therapeutic composition of the present invention comprising a cold-adapted equine influenza virus having a dominant interference phenotype to ameliorate or reduce disease symptoms in an animal previously inoculated or susceptible to inoculation with a virulent, wild-type equine influenza virus can be tested by screening for the reduction or absence of disease symptoms in the treated animal.

The present invention also includes methods to produce a therapeutic composition of the present invention. Suitable and preferred methods for making a therapeutic composition of the present invention are disclosed herein. Pertinent steps involved in producing one type of therapeutic composition of the present invention, i.e., a cold-adapted equine influenza virus, include (a) passaging a wild-type equine influenza virus in vitro, for example, in embryonated chicken eggs; (b) selecting viruses that grow at a reduced temperature; (c) repeating the passaging and selection steps one or more times, at progressively lower temperatures, until virus populations are selected which stably grow at the desired lower temperature; and (d) mixing the resulting virus preparation with suitable excipients.

The pertinent steps involved in producing another type of therapeutic composition of the present invention, i.e., a reassortant influenza A virus having at least one genome segment of an equine influenza virus generated by adaptation, includes the steps of (a) mixing the genome segments of a donor cold-adapted equine influenza virus, which preferably also has the phenotypes of attenuation, temperature sensitivity, or dominant interference, with the genome segments of a recipient influenza A virus, and (b) selecting reassortant viruses that have at least one identifying phenotype of the donor equine influenza virus. Identifying phenotypes to select for include attenuation, cold-adaptation, temperature sensitivity, and dominant interference. Methods to screen for these phenotypes are well known to those skilled in the art, and are disclosed herein. It is preferable to screen for viruses that at least have the phenotype of attenuation.

Using this method to generate a reassortant influenza A virus having at least one genome segment of a equine influenza virus generated by cold-adaptation, one type of reassortant virus to select for is a "6+2" reassortant, where the six "internal gene segments," i.e., those coding for the NP, PB2, PB1, PA, M, and NS genes, are derived from the donor cold-adapted equine influenza virus genome, and the two "external gene segments," i.e., those coding for the HA and NA genes, are derived from the recipient influenza A virus. A resultant virus thus produced can have the cold-adapted, attenuated, temperature sensitive, and/or interference phenotypes of the donor cold-adapted equine influenza virus, but the antigenicity of the recipient strain.

The following examples are provided for the purposes of illustration and are not intended to limit the scope of the present invention.

EXAMPLE 1

This example discloses the production and phenotypic characterization of several cold-adapted equine influenza viruses of the present invention.

A. Parental equine influenza virus, A/equine/Kentucky/1/91 (H3N8) (obtained from Tom Chambers, the University of Kentucky, Lexington, Ky.) was subjected to cold-adaptation in a foreign host species, i.e., embryonated chicken eggs, in the following manner. Embryonated, 10 or 11-day old chicken eggs, available, for example, from Truslow Farms, Chestertown, Md. or from HyVac, Adel, Iowa, were inoculated with the parental equine influenza virus by injecting about 0.1 milliliter (ml) undiluted AF containing approximately $10^6$ plaque forming units (pfu) of virus into the allantoic cavity through a small hole punched in the shell of the egg. The holes in the eggs were sealed with nail polish and the eggs were incubated in a humidified incubator set at the appropriate temperature for three days. Following incubation, the eggs were candled and any non-viable eggs were discarded. AF was harvested from viable embryos by aseptically removing a portion of the egg shell, pulling aside the chorioallantoic membrane (CAM) with sterile forceps and removing the AF with a sterile pipette. The harvested AF was frozen between passages. The AF was then used, either undiluted or diluted 1:1000 in phosphate-buffered saline (PBS) as noted in Table 1, to inoculate a new set of eggs for a second passage, and so on. A total of 69 passages were completed. Earlier passages were done at either about 34° C. (passages 1–2) or about 30° C. and on subsequent passages, the incubation temperature was shifted down either to about 28° C., or to about 26° C. In order to increase the possibility of the selection of the desired phenotype of a stable, attenuated virus, the initial serial passage was expanded to included five different limbs of the serial passage tree, A through E, as shown in Table 1.

TABLE 1

Passage history of the limbs A through E

| Temperature | Passage # | | | | |
|---|---|---|---|---|---|
| | Limb A | Limb B | Limb C | Limb D | Limb E |
| 34° C. | 1–2 | 1–2 | 1–2 | 1–2 | 1–2 |
| 30° C. | 3–8 | 3–29 | 3–29 | 3–29 | 3–29 |
| 28° C. | | 30–33* | 30–68* | 30–33 | 30–69 |
| 26° C. | 9–65 | 34–69* | | 34–65 | |

*the infectious allantoic fluid was diluted 1:1000 in these passages

B. Virus isolates carried through the cold-adaptation procedure described in section A were tested for temperature sensitivity, i.e., a phenotype in which the cold-adapted virus grows at the lower, or permissive temperature (e.g., about 34° C.), but no longer forms plaques at a higher, or non-permissive temperature (e.g., about 37° C. or about 39° C.), as follows. At each cold-adaptation passage, the AF was titered by plaque assay at about 34° C. Periodically, individual plaques from the assay were clonally isolated by excision of the plaque area and placement of the excised agar plug in a 96-well tray containing a monolayer of MDCK cells. The 96-well trays were incubated overnight and the yield assayed for temperature sensitivity by CPE assay in duplicate 96-well trays incubated at about 34° C. and at about 39° C. The percent of the clones that scored as temperature sensitive mutants by this assay, i.e., the number of viral plaques that grew at 34° C. but did not grow at 39° C., divided by the total number of plaques, was calculated, and is shown in Table 2. Temperature sensitive isolates were then evaluated for protein synthesis at the non-permissive temperature by visualization of radiolabeled virus-synthesized proteins by SDS polyacrylamide gel electrophoresis (SDS-PAGE).

TABLE 2

Percent of isolated Clones that were temperature sensitive.

| | Percent Temperature Sensitive | | | | |
|---|---|---|---|---|---|
| Passage# | Limb A | Limb B | Limb C | Limb D | Limb E |
| p36 | 56% | 66% | 0% | 66% | 54% |
| p46 | | 80% | 60% | | 75% |
| p47 | | | 80% | | |
| p48 | | | 100% | | |
| p49 | | 100% | | 100% | 50% |
| p50 | | | 90% | | |
| p51 | | 100% | | | |
| p52 | | | | | 57% |
| p62 | 100% | | | 100% | |
| p65 | | | 100% | | |
| p66 | | 100% | | | 88% |

From the clonal isolates tested for temperature sensitivity, two were selected for further study. Clone EIV-P821 was selected from the 49th passage of limb B and clone EIV-P824 was selected from the 48th passage of limb C, as defined in Table 1. Both of these virus isolates were temperature sensitive, with plaque formation of both isolates inhibited at by temperature of about 39° C. At this temperature, protein synthesis was complelely inhibited by EIV-P821, but EIV-P824 exhibited normal levels of protein synthesis. In addition, plaque formation by EIV-P821 was inhibited at a temperature of about 37° C., and at this temperature, late gene expression was inhibited, i.e., normal levels of NP protein were synthesized, reduced or no M1 or HA proteins were synthesized, and enhanced levels of the polymerase proteins were synthesized. The phenotype observed at 37° C., being typified by differential viral protein synthesis, was distinct from the protein synthesis phenotype seen at about 39° C., which was typified by the inhibition of synthesis of all viral proteins. Virus EIV-P821 has been deposited with the American Type Culture Collection (ATCC) under Accession No. ATCC VR-2625, and virus EIV-P824 has been deposited with the ATCC under Accession No. ATCC VR-2624.

C. Further characterization of the mutations in isolate EIV-P821 were carried out by reassortment analysis, as follows. Reassortment analysis in influenza viruses allows one skilled in the art, under certain circumstances, to correlate phenotypes of a given virus with putative mutations occurring on certain of the eight RNA segments that comprise an influenza A virus genome. This technique is described, for example, in Palese, et al., ibid. A mixed infection of EIV-P821 and an avian influenza virus, A/mallard/New York/6750/78 was performed as follows. MDCK cells were co-infected with EIV-P821 at a multiplicity of infection (MOI) of 2 pfu/cell and A/mallard/New York/6750/78 at an MOI of either 2, 5, or 10 pfu/cell. The infected cells were incubated at a temperature of about 34° C. The yields of the various co-infections were titered and individual plaques were isolated at about 34° C., and the resultant clonal isolates were characterized as to whether they were able to grow at about 39° C. and about 37° C., and express their genes, i.e., synthesize viral proteins, at about 39° C., about 37° C., and about 34° C. Protein synthesis was evaluated by SDS-PAGE analysis of radiolabeled infected-cell lysates. The HA, NP and NS-1 proteins of the two parent viruses, each of which is encoded by a separate genome segment, were distinguishable by SDS-PAGE analysis, since these particular viral proteins, as derived from either the equine or the avian influenza virus, migrate at different apparent molecular weights. In this way it was possible, at least for the HA, NP, and NS-1 genes, to evaluate whether certain phenotypes of the parent virus, e.g., the temperature sensitive and the protein synthesis phenotypes, co-segregate with the genome segments carrying these genes. The results of the reassortment analyses investigating co-segregation of a) the mutation inhibiting plaque formation, i.e., the induction of CPE, at a non-permissive temperature of about 39° C. or b) the mutation inhibiting protein synthesis at a non-permissive temperature of about 39° C. with each of the EIV-P821 HA, NP and NS-1 proteins are shown in Tables 3 and 4, respectively.

TABLE 3

Reassortment analysis of the BIV-P821 39° C. plaque formation phenotype with avian influenza virus, A/mallard/New York/6750/78

| Gene | Virus | ts+[1] | ts−[2] |
|---|---|---|---|
| HA | avian | 26 | 13 |
|  | equine | 11 | 44 |
| NP | avian | 37 | 8 |
|  | equine | 0 | 49 |
| NS-1 | avian | 9 | 8 |
|  | equine | 12 | 20 |

[1]number of clonal isolates able to induce CPE in tissue culture cells at a temperature of about 39° C.
[2]number of clonal isolates inhibited in the ability to induce CPE in tissue culture cells at a temperature of about 39° C.

TABLE 4

Reassortment analysis of the EIV-P821 39° C. protein synthesis phenotype with avian influenza virus, A/mallard/New York/6750/78

| Gene | Virus | ts+[1] | ts−[2] |
|---|---|---|---|
| HA | avian | 18 | 1 |
|  | equine | 11 | 7 |
| NP | avian | 34 | 5 |
|  | equine | 7 | 8 |
| NS-1 | avian | 10 | 4 |
|  | equine | 14 | 5 |

[1]number of clonal isolates which synthesize all viral proteins at a temperature of about 39° C.
[2]number of clonal isolates inhibited in the ability to synthesize all viral proteins at a temperature of about 39° C.

The results demonstrated an association of the equine NP gene with a mutation causing the inability of EIV-P821 to form plaques at a non-permissive temperature of about 39° C., but the results did not suggest an association of any of the HA, NP, or NS-1 genes with a mutation causing the inability of EIV-P821 to express viral proteins at a non-permissive temperature of about 39° C. Thus, these data also demonstrated that the plaque formation phenotype and the protein synthesis phenotype observed in virus EIV-P821 were the result of separate mutations.

D. Studies were also conducted to determine if cold-adapted equine influenza viruses of the present invention have a dominant interference phenotype, that is, whether they dominate in mixed infection with the wild type parental virus A/Kentucky/1/91 (H3N8). The dominant interference phenotype of viruses EIV-P821 and EIV-P824 were evaluated in the following manner. Separate monolayers of MDCK cells were singly infected with the parental virus A/Kentucky/1/91 (H3N8) at an MOI of 2, singly infected with either cold-adapted virus EIV-P821 or EIV-P824 at an MOI of 2, or simultaneously doubly infected with both the parental virus and one of the cold adapted viruses at an MOI of 2+2, all at a temperature of about 34° C. At 24 hours after infection, the media from the cultures were harvested and the virus yields from the various infected cells were measured by duplicate plaque assays performed at temperatures of about 34° C. and about 39° C. This assay took advantage of the fact that cold adapted equine influenza viruses EIV-P821 or EIV-P824 are temperature sensitive and are thus unable to form plaques at a non-permissive temperature of about 39° C., while the parental virus is able to form plaques at both temperatures, thus making it possible to measure the growth of the parental virus in the presence of the cold adapted virus. Specifically, the dominant interference effect of the cold adapted virus on the growth of the parental virus was quantitated by comparing the virus yield at about 39° C. of the cells singly infected with parental virus to the yield of the parental virus in doubly infected cells. EIV-P821, in mixed infection, was able to reduce the yield of the parental virus by approximately 200 fold, while EIV-P824, in mixed infection, reduced the yield of the parental virus by approximately 3200 fold. This assay therefore showed that cold-adapted equine influenza viruses EIV-P821 and EIV-P824 both exhibit the dominant interference phenotype.

E. Virus isolate EIV-MSV+5 was derived from EIV-P821, as follows. EIV-P821 was passaged once in eggs, as described above, to produce a Master Seed Virus isolate, denoted herein as EIV-MSV0. EIV-MSV0 was then subjected to passage three additional times in eggs, the virus isolates at the end of each passage being designated EIV-MSV+1, EIV-MSV+2, and EIV-MSV+3, respectively. EIV-MSV+3 was then subjected to two additional passages in MDCK cells, as follows. MDCK cells were grown in 150 cm² tissue culture flasks in MEM tissue culture medium with Hanks Salts, containing 10% calf serum. The cells were then washed with sterile PBS and the growth medium was replaced with about 8 ml per flask of infection medium (tissue culture medium comprising MEM with Hanks Salts, 1 μg/ml TPCK trypsin solution, 0.125% bovine serum albumin (BSA), and 10 mM HEPES buffer). MDCK cells were inoculated with AF containing virus EIV-MSV+3 (for the first passage in MDCK cells) or virus stock harvested from EIV-MSV+4 (for the second passage in MDCK cells), and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer, resulting in virus isolates EIV-MSV+4 (the first passage in MDCK cells), and EIV-MSV+5 (the second passage in MDCK cells).

Viruses EIV-MSV0 and EIV-MSV+5 were subjected to phenotypic analysis, as described in section B above, to determine their ability to form plaques and synthesize viral proteins at temperatures of about 34° C., about 37° C., and about 39° C. Both EIV-MSV0 and EIV-MSV+5 formed plaques in tissue culture cells at a temperature of about 34° C., and neither virus isolate formed plaques or exhibited detectable viral protein synthesis at a temperature of about 39° C. Virus EIV-MSV0 had a similar temperature sensitive phenotype as EIV-PS821 at a temperature of about 37° C., i.e., it was inhibited in plaque formation, and late gene expression was inhibited. However, EIV-MSV+5, unlike its parent virus, EIV-P821, did form plaques in tissue culture at a temperature of about 37° C., and at this temperature, the virus synthesized normal amounts of all proteins. Virus EIV-MSV+5 has been deposited with the ATCC under Accession No. ATCC VR-2627.

EXAMPLE 2

Therapeutic compositions of the present invention were produced as follows.

A. A large stock of EIV-P821 was propagated in eggs as follows. About 60 specific pathogen-free embryonated chicken eggs were candled and non-viable eggs were discarded. Stock virus was diluted to about $1.0 \times 10^5$ pfu/ml in sterile PBS. Virus was inoculated into the allantoic cavity of the eggs as described in Example 1A. After a 3-day incubation in a humidified chamber at a temperature of about 34° C., AF was harvested from the eggs according to the method described in Example 1A. The harvested AF was mixed with a stabilizer solution, for example A1/A2 stabilizer, available from Diamond Animal Health, Des Moines, Iowa, at 25% V/V (stabilizer/AF). The harvested AF was batched in a centrifuge tube and was clarified by centrifugation for 10 minutes at 1000 rpm in an IEC Centra-7R refrigerated table top centrifuge fitted with a swinging bucket rotor. The clarified fluid was distributed into 1-ml cryovials and was frozen at about −70° C. Virus stocks were titrated on MDCK cells by CPE and plaque assay at about 34° C.

B. A large stock of EIV-P821 was propagated in MDCK cells as follows. MDCK cells were grown in 150 $cm^2$ tissue culture flasks in MEM tissue culture medium with Hanks Salts, containing 10% calf serum. The cells were then washed with sterile PBS and the growth medium was replaced with about 8 ml per flask of infection medium. The MDCK cells were inoculated with virus stock at an MOI ranging from about 0.5 pfu per cell to about 0.005 pfu per cell, and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer and stabilizer solution was added to the flasks at 25% V/V (stabilizer/virus solution). The supernatants were distributed aseptically into cryovials and frozen at −70° C.

C. Therapeutic compositions comprising certain cold-adapted temperature sensitive equine influenza viruses of the present invention were formulated as follows. Just prior to vaccination procedures, such as those described in Examples 3–7 below, stock vials of EIV-P821 or EIV-MSV +5 were thawed and were diluted in an excipient comprising either water, PBS, or in MEM tissue culture medium with Hanks Salts, containing 0.125% bovine serum albumin (BSA-MEM solution) to the desired dilution for administration to animals. The vaccine compositions were held on ice prior to vaccinations. All therapeutic compositions were titered on MDCK cells by standard methods just prior to vaccinations and wherever possible, an amount of the composition, treated identically to those administered to the animals, was titered after the vaccinations to ensure that the virus remained viable during the procedures.

EXAMPLE 3

A therapeutic composition comprising cold-adapted equine influenza virus EIV-P821 was tested for safety and its ability to replicate in three horses showing detectable prior immunity to equine influenza virus as follows. EIV-P821, produced as described in Example 1A, was grown in eggs as described in Example 2A and was formulated into a therapeutic composition comprising $10^7$ pfu EIV-P821/2 ml BSA-MEM solution as described in Example 2C.

Three ponies having prior detectable hemagglutination inhibition (HAI) titers to equine influenza virus were inoculated with a therapeutic composition comprising EIV-P821 by the following method. Each pony was given a 2-ml dose of EIV-P821, administered intranasally using a syringe fitted with a blunt cannula long enough to reach past the false nostril, 1 ml per nostril.

The ponies were observed for approximately 30 minutes immediately following and at approximately four hours after vaccination for immediate type allergic reactions such as sneezing, salivation, labored or irregular breathing, shaking, anaphylaxis, or fever. The animals were further monitored on days 1–11 post-vaccination for delayed type allergic reactions, such as lethargy or anorexia. None of the three ponies in this study exhibited any allergic reactions from the vaccination.

The ponies were observed daily, at approximately the same time each day, starting two days before vaccination and continuing through day 11 following vaccination for clinical signs consistent with equine influenza. The ponies were observed for nasal discharge, ocular discharge, anorexia, disposition, heart rate, capillary refill time, respiratory rate, dyspnea, coughing, lung sounds, presence of toxic line on upper gum, and body temperature. In addition submandibular and parietal lymph nodes were palpated and any abnormalities were described. None of the three ponies in this study exhibited any abnormal reactions or overt clinical signs during the observation period.

To test for viral shedding in the animals, on days 0 through 11 following vaccination, nasopharyngeal swabs were collected from the ponies as described in Chambers, et al., 1995, *Equine Practice*, 17, 19–23. Chambers, et al., ibid., is incorporated herein by reference in its entirety. Briefly, two sterile Dacron polyester tipped applicators (available, e.g., from Hardwood Products Co., Guilford, Me.) were inserted, together, into each nostril of the ponies. The swabs (four total, two for each nostril) were broken off into a 15-ml conical centrifuge tube containing 2.5 ml of chilled transport medium comprising 5% glycerol, penicillin, streptomycin, neomycin, and gentamycin in PBS at physiological pH. Keeping the samples on wet ice, the swabs were aseptically wrung out into the medium and the nasopharyngeal samples were divided into two aliquots. One aliquot was used to attempt isolation of EIV by inoculation of embryonated eggs, using the method described in Example 1. The AF of the inoculated eggs was then tested for its ability to cause hemagglutination, by standard methods, indicating the presence of equine influenza virus in the AF. On days 2 and 3 post-vaccination, the other aliquots were tested for virus by the Directigen® Flu A test, available from Becton-Dickinson (Cockeysville, Md.).

Attempts to isolate EIV from the nasopharyngeal secretions of the three animals by egg inoculation were unsuccessful. However on days 2 and 3, all animals tested positive for the presence of virus shedding using the Directigen Flu A test, consistent with the hypothesis that EIV-P821 was replicating in the seropositive ponies.

To test the antibody titers to EIV in the inoculated animals described in this example, as well as in the animals described in Examples 4–7, blood was collected from the animals prior to vaccination and on designated days post-vaccination. Serum was isolated and was treated either with trypsin/periodate or kaolin to block the nonspecific inhibitors of hemagglutination present in normal sera. Serum samples were tested for hemagglutination inhibition (HAI) titers against a recent EIV isolate by standard methods, described, for example in the "Supplemental assay method for conducting the hemagglutination inhibition assay for equine influenza virus antibody" (SAM 124), provided by the U.S.D.A. National Veterinary Services Laboratory under 9 CFR 113.2, which is incorporated by reference herein in its entirety.

The HAI titers of the three ponies are shown in Table 5. As can be seen, regardless of the initial titer, the serum HAI titers increased at least four-fold in all three animals after vaccination with EIV-P821.

These data demonstrate that cold-adapted equine influenza virus EIV-P821 is safe and non-reactogenic in seropositive ponies, and that these animals exhibited an increase in antibody titer to equine influenza virus, even though they had prior demonstrable titers.

TABLE 5

HAI titers of vaccinated animals*

| Animal ID | HAI Titer (days after vaccination) | | | |
|---|---|---|---|---|
| | 0 | 7 | 14 | 21 |
| 18 | 40 | 80 | 160 | 160 |
| 19 | 10 | 20 | 40 | 80 |
| 25 | 20 | 40 | 320 | 80 |

*HAI titers are expressed as the reciprocal of the highest dilution of serum which inhibited hemagglutination of erythrocytes by a recent isolate of equine influenza virus.

EXAMPLE 4

This Example discloses an animal study to evaluate the safety and efficacy of a therapeutic composition comprising cold-adapted equine influenza virus EIV-P821.

A therapeutic composition comprising cold-adapted equine influenza virus EIV-P821 was tested for attenuation, as well as its ability to protect horses from challenge with virulent equine influenza virus, as follows. EIV-P821, produced as described in Example 1, was grown in eggs as described in Example 2A and was formulated into a therapeutic composition comprising $10^7$ pfu of virus/2 ml water, as described in Example 2C. Eight EIV-seronegative ponies were used in this study. Three of the eight ponies were vaccinated with a 2-ml dose comprising $10^7$ pfu of the EIV-P821 therapeutic composition, administered intranasally, using methods similar to those described in Example 3. One pony was given $10^7$ pfu of the EIV-P821 therapeutic composition, administered orally, by injecting 6 ml of virus into the pharynx, using a 10-ml syringe which was adapted to create a fine spray by the following method. The protruding "seat" for the attachment of needles was sealed off using modeling clay and its cap was left in place. About 10 holes were punched through the bottom of the syringe, i.e., surrounding the "seat," using a 25-gauge needle. The syringe was placed into the interdental space and the virus was forcefully injected into the back of the mouth. The remaining four ponies were held as non-vaccinated controls.

The vaccinated ponies were observed for approximately 30 minutes immediately following and at approximately four hours after vaccination for immediate type allergic reactions, and the animals were further monitored on days 1–11 post-vaccination for delayed type allergic reactions, both as described in Example 3. None of the four vaccinated ponies in this study exhibited any abnormal reactions from the vaccination.

The ponies were observed daily, at approximately the same time each day, starting two days before virus vaccination and continuing through day 11 following vaccination for clinical signs, such as those described in Example 3. None of the four vaccinated ponies in this study exhibited any clinical signs during the observation period. This result demonstrated that cold-adapted equine influenza virus EIV-P821 exhibits the phenotype of attenuation.

To test for viral shedding in the vaccinated animals, on days 0 through 11 following vaccination, nasopharyngeal swabs were collected from the ponies as described in Example 3. The nasopharyngeal samples were tested for virus in embryonated chicken eggs according to the method described in Example 3.

As shown in Table 6, virus was isolated from only one vaccinated animal using the egg method. However, as noted in Example 3, the lack of isolation by this method does not preclude the fact that virus replication is taking place, since replication may be detected by more sensitive methods, e.g., the Directigen Flu A test.

TABLE 6

Virus isolation in eggs after vaccination

| Animal ID | Route | Virus Isolation (days after vaccination) | | | | | | | | | | | |
|---|---|---|---|---|---|---|---|---|---|---|---|---|---|
| | | 0 | 1 | 2 | 3 | 4 | 5 | 6 | 7 | 8 | 9 | 10 | 11 |
| 91 | IN | − | − | + | + | + | + | + | + | + | + | + | − |
| 666 | IN | − | − | − | − | − | − | − | − | − | − | − | − |
| 673 | IN | − | − | − | − | − | − | − | − | − | − | − | − |
| 674 | Oral | − | − | − | − | − | − | − | − | − | − | − | − |

To test the antibody titers to equine influenza virus in the vaccinated animals, blood was collected from the animals prior to vaccination and on days 7, 14, 21, and 28 post-vaccination. Serum samples were isolated and were tested for hemagglutination inhibition (HAI) titers against a recent EIV isolate according to the methods described in Example 3.

The HAI titers of the four vaccinated ponies are shown in Table 7.

TABLE 7

HAI titers after vaccination

| Animal ID | Route | HAI Titer (days after vaccination) | | | | |
|---|---|---|---|---|---|---|
| | | 0 | 7 | 14 | 21 | 28 |
| 91 | IN | <10 | <10 | <10 | <10 | <10 |
| 666 | IN | 10 | 10 | 10 | 20 | 20 |
| 673 | IN | 10 | 10 | 10 | 20 | 20 |
| 674 | Oral | 20 | 40 | 40 | 40 | 40 |

Unlike the increase in HAI titer observed with the three animals described in the study in Example 3, the animals in this study did not exhibit a significant increase, i.e., greater than four-fold, in HAI titer following vaccination with EIV-P821.

Approximately four and one-half months after vaccine virus administration, all 8 ponies, i.e., the four that were vaccinated and the four non-vaccinated controls, were challenged by the following method. For each animal, $10^7$ pfu of the virulent equine influenza virus strain A/equine/Kentucky/1/91 (H3N8) was suspended in 5 ml of water. A mask was connected to a nebulizer, and the mask was placed over the animal's muzzle, including the nostrils. Five (5) ml was nebulized for each animal, using settings such that it took 5–10 minutes to deliver the full 5 ml. Clinical observations, as described in Example 3, were performed on all animals three days before challenge and daily for 11 days after challenge.

Despite the fact that the vaccinated animals did not exhibit marked increases in their HAI titers to equine influenza virus, all four vaccinated animals were protected against equine influenza virus challenge. None of the vaccinated animals showed overt clinical signs or fever, although one of the animals had a minor wheeze for two days. On the other hand, all four non-vaccinated ponies shed virus and developed clinical signs and fever typical of equine influenza virus infection. Thus, this example demonstrates that a therapeutic composition of the present invention can protect horses from equine influenza disease.

EXAMPLE 5

This Example discloses an additional animal study to evaluate attenuation of a therapeutic composition comprising cold-adapted equine influenza virus EIV-P821, and its ability to protect vaccinated horses from subsequent challenge with virulent equine influenza virus. Furthermore, this study evaluated the effect of exercise stress on the safety and efficacy of the therapeutic composition.

A therapeutic composition comprising cold-adapted equine influenza virus EIV-P821 was tested for safety and efficacy in horses, as follows. EIV-P821, produced as described in Example 1, was grown in eggs as described in Example 2A and was formulated into a therapeutic composition comprising $10^7$ pfu virus/5 ml water, as described in Example 2C. Fifteen ponies were used in this study. The ponies were randomly assigned to three groups of five animals each, as shown in Table 8, there being two vaccinated groups and one unvaccinated control group. The ponies in group 2 were exercise stressed before vaccination, while the ponies in vaccinate group 1 were held in a stall.

TABLE 8

Vaccination/challenge protocol

| Group | No. Ponies | Exercise | Vaccine | Challenge |
|---|---|---|---|---|
| 1 | 5 | — | Day 0 | Day 90 |
| 2 | 5 | Days −4 to 0 | Day 0 | Day 90 |
| 3 | 5 | — | — | Day 90 |

The ponies in group 2 were subjected to exercise stress on a treadmill prior to vaccination, as follows. The ponies were acclimated to the use of the treadmill by 6 hours of treadmill use at a walk only. The actual exercise stress involved a daily exercise regimen starting 4 days before and ending on the day of vaccination (immediately prior to vaccination). The treadmill exercise regimen is shown in Table 9.

TABLE 9

Exercise regimen for the ponies in Group 2

| Speed (m/sec) | Time (min.) | Incline (°) |
|---|---|---|
| 1.5 | 2 | 0 |
| 3.5 | 2 | 0 |
| 3.5 | 2 | 7 |
| 4.5† | 2 | 7 |
| 5.5† | 2 | 7 |
| 6.5† | 2 | 7 |
| 7.5† | 2 | 7 |
| 8.5† | 2 | 7 |
| 3.5 | 2 | 7 |
| 1.5 | 10 | 0† |

†Speed, in meters per second (m/sec) was increased for each animal every 2 minutes until the heart rate reached and maintained ≦200 beats per minute Groups 1 and 2 were given a therapeutic composition comprising $10^7$ pfu of EIV-P821, by the nebulization method described for the challenge described in Example 4. None of the vaccinated ponies in this study exhibited any immediate or delayed allergic reactions from the vaccination.

The ponies were observed daily, at approximately the same time each day, starting two days before vaccination and continuing through day 11 following vaccination for clinical signs, such as those described in Example 3. None of the vaccinated ponies in this study exhibited any overt clinical signs during the observation period.

To test for viral shedding in the vaccinated animals, before vaccination and on days 1 through 11 following vaccination, nasopharyngeal swabs were collected from the ponies as described in Example 3. The nasopharyngeal samples were tested for virus in embryonated chicken eggs according to the method described in Example 3. Virus was isolated from the vaccinated animals, i.e., Groups 1 and 2, as shown in Table 10.

TABLE 10

Virus isolation after vaccination

| Group | Animal ID | Exercise | Virus Isolation (days after vaccination) | | | | | | | | | | | |
|---|---|---|---|---|---|---|---|---|---|---|---|---|---|---|
| | | | 0 | 1 | 2 | 3 | 4 | 5 | 6 | 7 | 8 | 9 | 10 | 11 |
| 1 | 12 | No | − | − | + | + | + | + | + | − | + | + | − | − |
| | 16 | | − | − | + | + | + | + | + | − | − | − | − | − |
| | 17 | | − | − | + | + | + | + | + | + | + | − | + | − |
| | 165 | | − | − | − | − | − | − | − | − | − | − | − | − |
| | 688 | | − | − | − | − | − | + | − | + | − | − | − | − |
| 2 | 7 | Yes | − | − | − | + | + | + | + | − | − | − | − | − |
| | 44 | | − | − | − | − | − | − | − | − | − | − | − | − |
| | 435 | | − | − | + | + | + | + | − | − | − | − | − | − |
| | 907 | | − | − | − | + | − | + | + | − | − | − | − | − |
| | 968 | | − | − | − | − | − | + | − | + | − | − | − | − |

To test the antibody titers to equine influenza virus in the vaccinated animals, blood was collected prior to vaccination and on days 7, 14, 21, and 28 post-vaccination. Serum samples were isolated and were tested for HAI titers against a recent EIV isolate according to the methods described in Example 3. These titers are shown in Table 11.

TABLE 11

HAI titers after vaccination and after challenge on day 90

| Group | Animal ID | Day Post-vaccination | | | | | | | | | |
|---|---|---|---|---|---|---|---|---|---|---|---|
| | | −1 | 7 | 14 | 21 | 28 | 91 | 105 | 112 | 119 | 126 |
| 1 | 12 | <10 | <10 | <10 | <10 | <10 | <10 | 80 | 320 | 320 | 640 |
| 1 | 16 | <10 | <10 | 20 | 20 | <10 | <10 | 20 | 160 | 320 | 320 |
| 1 | 17 | <10 | <10 | 10 | 10 | 10 | 10 | 80 | 160 | 160 | 160 |
| 1 | 165 | <10 | <10 | 10 | 10 | 10 | 10 | 80 | 80 | 80 | 80 |
| 1 | 688 | <10 | <10 | 20 | 20 | 20 | 20 | 20 | 20 | 20 | 40 |
| 2 | 7 | <10 | <10 | 10 | 10 | <10 | <10 | 20 | 80 | 80 | 40 |
| 2 | 44 | <10 | <10 | 20 | 20 | 20 | 10 | 80 | 320 | 320 | 320 |
| 2 | 435 | <10 | <10 | 20 | 20 | 10 | <10 | 20 | 80 | 80 | 80 |
| 2 | 907 | <10 | <10 | 10 | 10 | 20 | 10 | 10 | 40 | 80 | 80 |
| 2 | 968 | <10 | <10 | <10 | <10 | <10 | <10 | 40 | 160 | 160 | 160 |
| 3 | 2 | | | | | | <10 | 80 | 640 | 640 | 320 |
| 3 | 56 | | | | | | <10 | 80 | 320 | 320 | 320 |
| 3 | 196 | | | | | | <10 | 20 | 160 | 80 | 80 |
| 3 | 198 | | | | | | 10 | 40 | 160 | 320 | 320 |
| 3 | 200 | | | | | | <10 | 20 | 80 | 80 | 40 |

Group Description
1 Vaccination only
2 Vaccination and Exercise
3 Control

On day 90 post vaccination, all 15 ponies were challenged with $10^7$ pfu of equine influenza virus strain A/equine/Kentucky/1/91 (H3N8) by the nebulizer method as described in Example 4. Clinical observations, as described in Example 3, were performed on all animals three days before challenge and daily for 11 days after challenge. There were no overt clinical signs observed in any of the vaccinated ponies. Four of the five non-vaccinated ponies developed fever and clinical signs typical of equine influenza virus infection.

Thus, this example demonstrates that a therapeutic composition of the present invention protects horses against equine influenza disease, even if the animals are stressed prior to vaccination.

EXAMPLE 6

This Example compared the infectivities of therapeutic compositions of the present invention grown in eggs and grown in tissue culture cells. From a production standpoint, there is an advantage to growing therapeutic compositions of the present invention in tissue culture rather than in embryonated chicken eggs. Equine influenza virus, however, does not grow to as high a titer in cells as in eggs. In addition, the hemagglutinin of the virus requires an extracellular proteolytic cleavage by trypsin-like proteases for infectivity. Since serum contains trypsin inhibitors, virus grown in cell culture must be propagated in serum-free medium that contains trypsin in order to be infectious. It is well known by those skilled in the art that such conditions are less than optimal for the viability of tissue culture cells. In addition, these growth conditions may select for virus with altered binding affinity for equine cells, which may affect viral infectivity since the virus needs to bind efficiently to the animal's nasal mucosa to replicate and to stimulate immunity. Thus, the objective of the study disclosed in this example was to evaluate whether the infectivity of therapeutic compositions of the present invention was adversely affected by growth for multiple passages in in vitro tissue culture.

EIV-P821, produced as described in Example 1, was grown in eggs as described in Example 2A or in MDCK cells as described in Example 2B. In each instance, the virus was passaged five times. EIV-P821 was tested for its cold-adaptation and temperature sensitive phenotypes after each passage. The egg and cell-passaged virus preparations were formulated into therapeutic compositions comprising $10^7$ pfu virus/2 ml BSA-MEM solution, as described in Example 2C, resulting in an egg-grown EIV-P821 therapeutic composition and an MDCK cell-grown EIV-P821 therapeutic composition, respectively.

Eight ponies were used in this study. Serum from each of the animals was tested for HAI titers to equine influenza virus prior to the study. The animals were randomly assigned into one of two groups of four ponies each. Group A received the egg-grown EIV-P821 therapeutic composition, and Group B received the MDCK-grown EIV-P821 therapeutic composition, prepared as described in Example 2B. The therapeutic compositions were administered intranasally by the method described in Example 3.

The ponies were observed daily, at approximately the same time each day, starting two days before vaccination and continuing through day 11 following vaccination for allergic reactions or clinical signs as described in Example 3. No allergic reactions or overt clinical signs were observed in any of the animals.

Nasopharyngeal swabs were collected before vaccination and daily for 11 days after vaccination. The presence of virus material in the nasal swabs was determined by the detection of CPE on MDCK cells infected as described in Example 1, or by inoculation into eggs and examination of the ability of the infected AF to cause hemagglutination, as described in Example 3. The material was tested for the presence of virus only, and not for titer of virus in the sample. Virus isolation results are listed in Table 12. Blood was collected and serum samples from days 0, 7, 14, 21 and 28 after vaccination were tested for hemagglutination inhibition antibody titer against a recent isolate. HAI titers are also listed in Table 12.

TABLE 12

HAI titers and virus isolation after vaccination

| Group[2] | ID | HAI Titer (DPV[3]) | | | | | Virus Isolation (DPV[3]) | | | | | | | | | | | |
|---|---|---|---|---|---|---|---|---|---|---|---|---|---|---|---|---|---|---|
| | | 0 | 7 | 14 | 21 | 28 | 0 | 1 | 2 | 3 | 4 | 5 | 6 | 7 | 8 | 9 | 10 | 11 |
| 1 | 31 | <10 | 20 | 160 | 160 | 160 | — | EC | — | C | EC | EC | C | C | EC | — | — | — |
| | 37 | <10 | 40 | 160 | 160 | 160 | — | EC | C | C | EC | C | C | C | — | — | — | — |
| | 40 | <10 | 20 | 80 | 160 | 80 | — | EC | EC | C | — | C | EC | C | — | EC | EC | — |
| | 41 | <10 | 40 | 160 | 160 | 80 | — | EC | EC | C | EC | C | EC | EC | — | — | — | — |
| 2 | 32 | <10 | <10 | 80 | 80 | 40 | — | EC | — | C | — | C | — | C | — | EC | — | — |
| | 34 | <10 | 20 | 160 | 160 | 160 | — | EC | — | C | EC | C | EC | C | — | — | — | — |
| | 35 | <10 | <10 | 80 | 80 | 40 | — | EC | — | C | — | C | — | C | — | EC | — | — |
| | 42 | <10 | <10 | 80 | 80 | 40 | — | — | — | C | — | C | EC | EC | — | — | — | — |

[1]E = Egg isolation positive; C = CPE isolation positive; — = virus not detected by either of the methods
[2]Group 1: Virus passaged 5X in MDCK cells; Group 2: Virus passaged 5X in Eggs
[3]Days Post-vaccination The results in Table 12 show that there were no significant differences in infectivity or immunogenicity between the egg-grown and MDCK-grown EIV-P821 therapeutic compositions.

EXAMPLE 7

This example evaluated the minimum dose of a therapeutic composition comprising a cold-adapted equine influenza virus required to protect a horse from equine influenza virus infection.

The animal studies disclosed in Examples 3–6 indicated that a therapeutic composition of the present invention was efficacious and safe. In those studies, a dose of $10^7$ pfu, which correlates to approximately $10^8$ $TCID_{50}$ units, was used. However, from the standpoints of cost and safety, it is advantageous to use the minimum virus titer that will protect a horse from disease caused by equine influenza virus. In this study, ponies were vaccinated with four different doses of a therapeutic composition comprising a cold-adapted equine influenza virus to determine the minimum dose which protects a horse against virulent equine influenza virus challenge.

EIV-P821, produced as described in Example 1A, was passaged and grown in MDCK cells as described in Example 2B and was formulated into a therapeutic composition comprising either $2\times10^4$, $2\times10^5$, $2\times10^6$, or $2\times10^6$ $TCID_{50}$ units/1 ml BSA-MEM solution as described in Example 2C. Nineteen horses of various ages and breeds were used for this study. The horses were assigned to four vaccine groups, one group of three horses and three groups of four horses, and one control group of four horses (see Table 13). Each of the ponies in the vaccine groups were given a 1-ml dose of the indicated therapeutic composition, administered intranasally by methods similar to those described in Example 3.

TABLE 13

Vaccination protocol

| Group No. | No. Animals | Vaccine Dose, $TCID_{50}$ Units |
|---|---|---|
| 1 | 3 | $2 \times 10^7$ |
| 2 | 4 | $2 \times 10^6$ |
| 3 | 4 | $2 \times 10^5$ |
| 4 | 4 | $2 \times 10^4$ |
| 5 | 4 | control |

The ponies were observed for approximately 30 minutes immediately following and at approximately four hours after vaccination for immediate type reactions, and the animals were farther monitored on days 1–11 post-vaccination for delayed type reactions, both as described in Example 3. None of the vaccinated ponies in this study exhibited any abnormal reactions or overt clinical signs from the vaccination.

Blood for serum analysis was collected 3 days before vaccination, on days 7, 14, 21, and 28 after vaccination, and after challenge on Days 35 and 42. Serum samples were tested for HAI titers against a recent EIV isolate according to the methods described in Example 3. These titers are shown in Table 14. Prior to challenge on day 29, 2 of the 3 animals in group 1, 4 of the 4 animals in group 2, 3 of the 4 animals in group 3, and 2 of the 4 animals in group 4 showed at least 4-fold increases in HAI titers after vaccination. In addition, 2 of the 4 control horses also exhibited increases in HAI titers. One interpretation for this result is that the control horses were exposed to vaccine virus transmitted from the vaccinated horses, since all the horses in this study were housed in the same barn.

TABLE 14

HAI titers post-vaccination and post-challenge, and challenge results

| No. | Dose in $TCID_{50}$ units | Animal ID | Vaccination on Day 0, Challenge on Day 29 | | | | | | | Chall. Sick +/31 |
|---|---|---|---|---|---|---|---|---|---|---|
| | | | −1 | 7 | 14 | 21 | 28 | 35 | 42 | |
| 1 | $2 \times 10^7$ | 41 | <10 | <10 | 10 | 40 | 10 | 20 | 80 | – |
| | | 42 | 40 | 40 | 40 | 40 | 40 | <10 | 80 | – |
| | | 200 | <10 | <10 | 80 | 40 | 160 | 40 | 40 | – |
| 2 | $2 \times 10^6$ | 679 | <10 | 10 | 40 | 40 | 40 | 20 | 20 | – |
| | | 682 | <10 | <10 | 40 | 40 | 40 | 40 | 40 | – |
| | | 795 | 20 | 80 | 160 | 160 | 320 | 320 | 640 | – |
| | | R | <10 | 10 | 40 | 20 | 160 | 40 | 40 | – |

TABLE 14-continued

HAI titers post-vaccination and post-challenge, and challenge results

| No. | Dose in TCID$_{50}$ units | Animal ID | Vaccination on Day 0, Challenge on Day 29 | | | | | | | Chall. Sick +/31 |
|---|---|---|---|---|---|---|---|---|---|---|
| | | | −1 | 7 | 14 | 21 | 28 | 35 | 42 | |
| 3 | 2 × 10$^5$ | 73 | <10 | <10 | 160 | 40 | 80 | 160 | 160 | − |
| | | 712 | <10 | <10 | 20 | 20 | 40 | 40 | 20 | − |
| | | 720 | <10 | 20 | 80 | 40 | 80 | 80 | 160 | − |
| | | 796 | <10 | <10 | <10 | <10 | <10 | 10 | 80 | + |
| 4 | 2 × 10$^4$ | 75 | <10 | <10 | <10 | <10 | <10 | <10 | 160 | + |
| | | 724 | <10 | >10 | <10 | <10 | <10 | 20 | 320 | + |
| | | 789 | <10 | 10 | 320 | 160 | 320 | 320 | 320 | − |
| | | 790 | <10 | <10 | 80 | 40 | 160 | 80 | 40 | |
| 5 | Control | 12 | <10 | <10 | <10 | 20 | 20 | 40 | 40 | − |
| | | 22 | 10 | 20 | 40 | 10 | 160 | 40 | 640 | − |
| | | 71 | <10 | <10 | <10 | <10 | 10 | 20 | 160 | + |
| | | 74 | <10 | <10 | <10 | <10 | <10 | <10 | 20 | + |

On day 29 vaccination, all 19 ponies were challenged with equine influenza virus strain A/equine/Kentucky/1/91 (H3N8) by the nebulizer method as described in Example 4. The challenge dose was prospectively calculated to contain about 10$^8$ TCID$_{50}$ units of challenge virus in a volume of 5 ml for each animal. Clinical observations, as described in Example 3, were monitored beginning two days before challenge, the day of challenge, and for 11 days following challenge. As shown in Table 14, no animals in groups 1 or 2 exhibited clinical signs indicative of equine influenza disease, and only one out of four animals in group 3 became sick. Two out of four animals in group 4 became sick, and only two of the four control animals became sick. The results in Table 14 suggest a correlation between seroconversion and protection from disease, since, for example, the two control animals showing increased HAI titers during the vaccination period did not show clinical signs of equine influenza disease following challenge. Another interpretation, however, was that the actual titer of the challenge virus may have been less than the calculated amount of 10$^8$ TCID$_{50}$, units, since, based on prior results, this-level of challenge should have caused disease in all the control animals.

Nonetheless, the levels of seroconversion and the lack of clinical signs in the groups that received a therapeutic composition comprising at least 2×10$^6$ TCID$_{50}$ units of a cold-adapted equine influenza virus suggests that this amount was sufficient to protect a horse against equine influenza disease. Furthermore, a dose of 2×10$^5$ TCID$_{50}$ units induced seroconversion and gave clinical protection from challenge in 3 out of 4 horses, and thus even this amount may be sufficient to confer significant protection in horses against equine influenza disease.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

We claim:

1. A therapeutic composition to protect an animal against disease caused by an influenza A virus, comprising an excipient and a cold-adapted equine influenza A virus that grows at a temperature lower than about 34° C., wherein said virus replicates in embryonated chicken eggs at a temperature ranging from about 26° C. to about 30° C.

2. The therapeutic composition of claim 1, wherein said disease is caused by equine influenza virus, and wherein said therapeutic composition is administered prophylactically to an equid, thereby eliciting an immune response against equine influenza virus in said equid.

3. The therapeutic composition of claim 1, wherein said therapeutic composition comprises from about $10^5$ $TCID_{50}$ units to about $10^8$ $TCID_{50}$ units of said virus.

4. A method to protect an animal against disease caused by an influenza A virus comprising administering to said animal a therapeutic composition comprising a cold-adapted equine influenza A virus that grows at a temperature lower than about 34° C., wherein said virus replicates in embryonated chicken eggs at a temperature ranging from about 26° C. to about 30° C.

5. The method of claim 4, wherein said animal is an equid.

6. The method of claim 4, wherein said disease is caused by equine influenza virus, and wherein said therapeutic composition is administered prophylactically to an equid, thereby eliciting an immune response against equine influenza virus in said equid.

7. The method of claim 4, wherein said therapeutic composition is administered to said animal by a route that will allow virus entry into mucosal cells of the upper respiratory tract.

8. The method of claim 4, wherein said therapeutic composition further comprises an excipient.

9. The therapeutic composition of claim 1, wherein said virus is attenuated, such that administration of said virus to an animal results in reduced clinical signs of disease as compared to clinical signs observed in an animal infected with wild-type equine influenza virus.

10. The therapeutic composition of claim 1, wherein said virus is temperature sensitive, such that said virus does not replicate or form plaques in tissue culture cells at a temperature of about 39° C.

11. The therapeutic composition of claim 1, wherein said virus does not form plaques in tissue culture cells at a temperature of about 37° C.

12. The therapeutic composition of claim 1, wherein a phenotype comprising a non-permissive temperature of about 39° C. is conferred on said virus by at least two mutations in the genome of said virus, comprising a first mutation that inhibits plaque formation and a second mutation that inhibits protein synthesis.

13. The therapeutic composition of claim 12, wherein said first mutation co-segregates with the segment of said genome comprising the nucleoprotein gene of said virus.

14. The therapeutic composition of claim 12, further comprising at least one additional mutation, wherein said additional mutation confers a phenotype comprising a non-permissive temperature of about 37° C. on said virus, and wherein said phenotype is selected from the group consisting of inhibition of plaque formation at a temperature of about 37° C. and inhibition of the expression of the late genes of said virus at a temperature of about 37° C.

15. The therapeutic composition of claim 1, wherein said virus is produced by a method comprising the steps of:

a) passaging a wild-type equine influenza virus; and b) selecting viruses that grow at a reduced temperature.

16. The therapeutic composition of claim 15, wherein said virus is produced by a method further comprising repetition of said passaging and selection steps one or more times, wherein said reduced temperature is made progressively lower.

17. The therapeutic composition of claim 15, wherein said passaging step is carried out in embryonated chicken eggs.

18. The therapeutic composition of claim 1, wherein said virus comprises a dominant interference phenotype.

19. The therapeutic composition of claim 1, wherein said virus is a cold-adapted variant of equine influenza virus strain A/equine/Kentucky/1/91 (H3N8).

20. The therapeutic composition of claim 1, wherein said virus comprises the identifying phenotypes of a virus selected from the group consisting of: EIV-P821, identified by accession No. ATCC VR-2625; EIV-P824, identified by accession No. ATCC VR-2624; and MSV+5, identified by accession No. ATCC VR-2627.

21. The therapeutic composition of claim 1, wherein said virus is selected from the group consisting of: EIV-P821, identified by accession No. ATCC VR-2625; EIV-P824, identified by accession No. ATCC VR-2624; MSV+5, identified by accession No. ATCC VR-2627; and progeny of any of said viruses having any of said accession numbers.

22. The method of claim 4, wherein said virus is attenuated, such that administration of said virus to an animal results in reduced clinical signs of disease as compared to clinical signs observed in an animal infected with wild-type equine influenza virus.

23. The method of claim 4, wherein said virus is temperature sensitive, such that said virus does not replicate or form plaques in tissue culture cells at a temperature of about 39° C.

24. The method of claim 4, wherein said virus does not form plaques in tissue culture cells at a temperature of about 37° C.

25. The method of claim 4, wherein a phenotype comprising a non-permissive temperature of about 39° C. is conferred on said virus by at least two mutations in the genome of said virus, comprising a first mutation that inhibits plaque formation and a second mutation that inhibits protein synthesis.

26. The method of claim 25, wherein said first mutation co-segregates with the segment of said genome comprising the nucleoprotein gene of said virus.

27. The method of claim 25, further comprising at least one additional mutation, wherein said additional mutation confers a phenotype comprising a non-permissive temperature of about 37° C. on said virus, and wherein said phenotype is selected from the group consisting of inhibition of plaque formation at a temperature of about 37° C. and inhibition of the expression of the late genes of said virus at a temperature of about 37° C.

28. The method of claim 4, wherein said virus is produced by a method comprising the steps of:

a) passaging a wild-type equine influenza virus; and b) selecting viruses that grow at a reduced temperature.

29. The method of claim 28, wherein said virus is produced by a method further comprising repetition of said passaging and selection steps one or more times, wherein said reduced temperature is made progressively lower.

30. The method of claim 28, wherein said passaging step is carried out in embryonated chicken eggs.

31. The method of claim 4, wherein said virus comprises a dominant interference phenotype.

32. The method of claim 4, wherein said virus is a cold-adapted variant of equine influenza virus strain A/equine/Kentucky/1/91 (H3N8).

33. The method of claim 4, wherein said virus comprises the identifying phenotypes of a virus selected from the group consisting of: EIV-P821, identified by accession No. ATCC VR-2625; EIV-P824, identified by accession No. ATCC VR-2624; and MSV+5, identified by accession No. ATCC VR-2627.

34. The method of claim 4, wherein said virus is selected from the group consisting of: EIV-P821, identified by accession No. ATCC VR-2625; EIV-P824, identified by accession No. ATCC VR-2624; MSV+5, identified by accession No. ATCC VR-2627; and progeny of any of said viruses having any of said accession numbers.

* * * * *